(12) United States Patent
Xu et al.

(10) Patent No.: US 7,550,611 B2
(45) Date of Patent: Jun. 23, 2009

(54) CARBON NANOCHIPS AS CATALYST SUPPORTS FOR METALS AND METAL OXIDES

(75) Inventors: Xuejun Xu, Westborough, MA (US); R. Terry K. Baker, Hopkinton, MA (US)

(73) Assignee: Catalytic Materials, LLC, Pittsboro, NC (US)

( * ) Notice: Subject to any disclaimer, the term of this patent is extended or adjusted under 35 U.S.C. 154(b) by 802 days.

(21) Appl. No.: 10/952,696

(22) Filed: Sep. 29, 2004

(65) Prior Publication Data

US 2005/0084441 A1 Apr. 21, 2005

Related U.S. Application Data

(63) Continuation-in-part of application No. 10/712,247, filed on Nov. 13, 2003, now Pat. No. 6,913,740.

(60) Provisional application No. 60/426,198, filed on Nov. 14, 2002.

(51) Int. Cl.
C07D 301/10 (2006.01)

(52) U.S. Cl. .................... 549/534; 423/447.7; 423/488; 502/180; 502/184; 585/250; 205/413

(58) Field of Classification Search ............. 423/447.2, 423/447.7, 522, 448; 502/184, 180; 549/534; 205/413; 568/479; 564/422; 585/270, 250
See application file for complete search history.

(56) References Cited

U.S. PATENT DOCUMENTS

| | | | |
|---|---|---|---|
| 5,149,584 | A | 9/1992 | Baker et al. |
| 5,413,866 | A | 5/1995 | Baker et al. |
| 5,458,784 | A | 10/1995 | Baker et al. |
| 5,538,929 | A | 7/1996 | Sudhaker et al. |
| 5,569,635 | A | 10/1996 | Moy et al. |
| 5,618,875 | A | 4/1997 | Baker et al. |
| 5,653,951 | A | 8/1997 | Rodriguez et al. |
| 5,972,525 | A | 10/1999 | Mori et al. |
| 6,159,892 | A | 12/2000 | Moy et al. |
| 6,277,780 | B1 | 8/2001 | Beckler et al. |
| 6,537,515 | B1 | 3/2003 | Baker et al. |

OTHER PUBLICATIONS

E. Theodoridou, A.D. Jannakousakis, J. O. Besenhard and R. F. Sauter, "Carbon Fibre-Supported Noble Metal Catalysts: Optimization of Fibre Pretreatment", Synthetic Metals, 1986, pp. 125-135.
C. Pham-Huu, N. Keller, L. J. Chabonniere, R. Ziessel, and M. J. Ledoux, "Carbon Nanofiber Supported Palladium Catalyst for Liquid-Phase Reactions. An Active and Selective Catalyst for Hydrogenation of Cinnamaldehyde into Hydrocinnamaldehyde", Journal of Molecular Catalysis A: Chemical, vol. 170, May 2001, pp. 155-163.
M. S. Hoogenraad, R.A.G.M.M. van Leeuwarden, G. J. B van Breda Vriesman, A. Broersma, A. J. van Dillen and J.W. Geus, "Metal Catalysts supported on a Novel Carbon Support", Preparation of Catalysts VI, (G. Poncelet et al. Editors), 1995, pp. 263-271.
Colin Park and R. Terry K. Baker, "Catalytic Behavior of Graphite Nanofiber Supported Nickel Particles. 2. The Influence of the Nanofiber Structure", American Chemical Society, 1998.
Nelly M. Rodriguez, Myung-Soo Kim, and R. Terry K. Baker, "Carbon Nanfibers: A Unique Catalyst Support Medium", The Journal of Physical Chemistry, 1994, pp. 13108-13111.
E. Theodoridou, A. D. Jannakoudakis, J. O. Besenhard and R. F. Sauter, "Carbon Fibre-Supported Noble Metal Catalysts: Optimization of Fibre Pretreatment", Synthetic Metals 14, 1986, pp. 125-135.
C. Pham-Huu, N. Keller, Gabrielle Ehret, L. J. Charbonniere, R. Ziessel, and M. J. Ledoux, "Carbon Nanofiber Supported Palladium Catalyst for Liquid-Phase Reactions. An Active and Selective Catalyst for Hydrogenation of Cinnamaldehyde into Hydrocinnamaldehyde", Journal of Mollecular Catalysis A: Chemical, vol. 170, May 2001, pp. 155-163.
M. S. Hoogenraad, R.A.G.M.M. van Leeuwarden, G. J. B. van Breda Vriesman, A. Broersma, A. J. van Dillen and J. W. Geus, "Metal Catalysts supported on a Novel Carbon Support", Preparation of Catalysts VI, (G. Poncelet et al. Editors), 1995, pp. 263-271.
Colin Park and R. Terry K. Baker, "Catalytic Behavior of Graphite Nanofiber Supported Nickel Particles. 2. The Influence of the Nanofiber Structure", American Chemical Society, 1998.
Nelly M. Rodriguez, Myung-Soo Kim, and R. Terry K. Baker, "Carbon Nanofibers: A Unique Catalysts Support Medium", The Journal of Physical Chemistry, 1994, pp. 13108-13111.
Dresselhaus, et al., "Intercalation Compounds of Graphite", Advances in Physics, vol. 30, No. 2, pp. 139-169 and pp. 311-316 (1981).
Myung-Soo Kim, et al., "Carbon Nanofibers as a Novel Catalyst Support" Mat. Res. Soc. Symp. Proc. vol. 368, pp. 99-104, 1995.
Baker, et al., "Catalytic Growth of Carbon Nanofibers and Nanotubes;" Mas Res. Soc. Symp. Proc. vol. 349, pp. 251-256, 1994.
"The Catalytic Use of Onion-Like Carbon Materials for Styrene Synthesis by Oxidative Dehydrogenation of Ethylbenzene", Keller et al., Agnew Chem. Int. Ed., vol. 41 No. 11, pp. 1885-1888 (2002).
"Carbon Nanofiliments in Heterogeneous Catalysis: An Industrial Application for New Carbon Materials", Mestl, et al., Agnew Chem. Int. Ed., vol. 40 No. 11, 2066-2068 (2001).

*Primary Examiner*—Bernard Dentz
*Assistant Examiner*—David E Gallis
(74) *Attorney, Agent, or Firm*—Henry E. Naylor; Kean Miller Hawthorne D'Armond McCowan & Jarman, LLP

(57) ABSTRACT

High temperature treatment of graphite nanofibers to convert the materials to carbon nanochips and thereby enhance their performance as support media for metal catalytic particles. The carbon nanochips are suitable for supports for metal and metal oxide particles to catalyze chemical reactions such as oxidation, hydrogenation, oxidative-dehydrogenation, and dehydrogenation. In this regard, they function as a new type of highly conductive catalyst support media.

5 Claims, No Drawings

CARBON NANOCHIPS AS CATALYST SUPPORTS FOR METALS AND METAL OXIDES

CROSS REFERENCE TO RELATED APPLICATIONS

This is a Continuation-in-Part of U.S. Ser. No. 10/712,247 filed Nov. 13, 2003 now U.S. Pat. No. 6,913,740 which is based on Provisional Application U.S. Ser. No. 60/426,198 filed Nov. 14, 2002.

FIELD OF THE INVENTION

This invention relates to the use of carbon nanochips, which are formed from high temperature treatment of "platelet" and "herringbone" graphite nanofibers, as novel catalyst supports for metals and metal oxide particles. The carbon nanochips are suitable for use as a new type of highly conductive catalyst support media. These new supported metal and metal oxide systems are suitable for catalyzing reactions such as oxidation, hydrogenation, reforming, steam reforming, oxidative dehydrogenation, dehydrogenation, isomerization, carbonylation, decarbonylation and electro-catalytic reactions.

BACKGROUND OF THE INVENTION

The unusual arrangement of the surface carbon atoms encountered in graphite nanofibers comprised of graphite sheets (platelets) aligned at an angle not parallel to the longitudinal axis of the nanofiber, offer some unique methods to control the structure of supported catalytic metal particles and induce major changes in their catalytic performance. Graphitic nanofibers comprised of graphite platelets aligned substantially perpendicular to the longitudinal axis are sometimes referred as "platelet" nanofibers herein. Graphitic nanofibers that are aligned at an angle not perpendicular and not parallel are sometimes referred to as "herringbone" nanofibers. It is possible to use such nanofibers as templates for the vapor deposition of metal oxides that are likely to grow in an epitaxial format on the substrate surface. A number of investigations have focused on the modifications in both particle morphology and catalytic performance brought about by supporting metal crystallites on carbon nanofibers (Rodriguez et al. 1994, Hoogenraad et al. 1995, Chambers et al. 1998, Park and Baker 1998). The exposed surfaces of some of these materials consist entirely of graphite edges that are separated by a distance of about 0.335 nm. Such a feature provide a template for the deposition of metal crystallites where the surface atoms adopt arrangements that are not generally encountered on conventional support media, such as active carbon, silica or gamma-alumina.

Experiments performed with nickel particles supported on graphite nanofibers showed that such systems exhibited unusual properties with regard to the selectivity patterns obtained for the hydrogenation of olefins and diolefins when compared to the behavior found when the metal was dispersed on conventional oxide carriers, such as alumina (Rodriguez et al. 1994, Chambers et al. 1998, Park and Baker 1998). This enhancement in both activity and selectivity was attributed to the fact that the nickel crystallites were located on the edge sites of the nanofibers and as a consequence, the arrangement of the metal atoms was governed by the interaction with the carbon atoms in these regions. Under such circumstances, one might expect different crystallographic faces of nickel to be exposed to the reactant gas compared to those present when the metal was dispersed on less ordered materials. This claim was supported by the observations from high-resolution transmission electron microscopy examinations, which revealed the existence of major differences in the morphological characteristics of metal particles supported on graphite nanofibers and gamma-alumina. Close inspection of the metal particles supported on graphite nanofibers showed that they were preferentially aligned with respect to the fiber lattice. Furthermore, the hexagonal-shaped crystallites were very thin and flat, features consistent with the existence of a strong metal-support interaction. It was also suggested that the interaction between the conductive graphite nanofibers and the metal particles was responsible for inducing electronic perturbations in the latter entities that were beneficial with regard to enhancing the catalytic performance of the system.

U.S. Pat. No. 6,485,858 B1 to Baker et al. teaches the use of Pt supported on graphite nanofibers as a catalyst for use in fuel cell electrodes. A 5-wt. % Pt dispersion on the graphite nanofibers was found to give a comparable performance to a 30 wt. % Pt loading on XC-72 Vulcan carbon for the electrochemical oxidation of methanol at 80° C. U.S. Pat. Nos. 5,569,635 and 6,159,892 to Moy et al. teach the use of carbon fibrils (also known as cylindrical multi-walled carbon nanotubes) as catalyst supports. In contrast to "platelet" and "herring-bone" graphite nanofibers, the surface of carbon fibrils (substantially cylindrical nanotubes) consist of graphite basal planes and not edges. When metal or metal oxide particles are dispersed on conventional carbon materials, conventional graphite materials or conventional cylindrical carbon nanotubes, they typically exhibit relatively weak interactions with the basal plane regions of the carbon resulting in the formation of relatively large globular entities (like oil or water droplets). Most of the metal and metal oxide atoms are contained in the globular entities and are consequently unavailable to perform the desired catalytic reaction. It would be highly desirable if the catalytic particles could be deposited in such a manner that they were spread in the form of a thin film over the surface of the carbon. The resulting catalyst-containing structure would give rise to the most efficient use of the catalytic metal or metal oxide and as a consequence, it would be possible to not only optimize the catalytic efficiency of the system, but it would be also possible to reduce the catalyst loading. This condition can be achieved when the metal or metal oxide particles are dispersed on the highly tailored surfaces of "platelet" and "herring-bone" graphite nanofibers.

While significant benefits can be realized by controlling the structural features of metal and metal oxide particles as a result of dispersing such entities on the surface edge sites of "platelet" and "herring-bone" graphite nanofibers, further improvements in catalytic performance are required. In this context, major advances can be achieved if one is not only able to control the morphological characteristics, but also to simultaneously regulate the electronic properties of the supported particles by using a highly tailored conductive support medium. There remains a need in the art for a carbon support material that combines the attributes of the "platelet" and "herring-bone" graphitic nanofibers and which possess high electrical conductivity.

SUMMARY OF THE INVENTION

In accordance with the present invention there is provided a catalytic chemical process selected from oxidation, hydrogenation, reforming, steam reforming, oxidative dehydrogenation, dehydrogenation, isomerization, carbonylation, decarbonylation and electro-catalytic, which chemical process is catalyzed by a catalyst composition comprised of at least one metal or metal oxide selected from the metals from Groups VIII, IB, and IIB of the Periodic Table of the Elements, supported on graphitic nanofibers which nanofibers are comprised of a plurality of graphite platelets aligned perpendicular, or at an angle, other than parallel, to the longitudinal axis of the nanostructure, wherein at least about 50% of the edge sites of said nanofibers are exposed, and wherein said graphite nanofibers, prior to use in said catalytic process are heat treated in the presence of an inert gas at temperatures from about 2300° C. to about 3000° C.

DETAILED DESCRIPTION OF THE INVENTION

The catalyst support materials of the present invention are referred to as carbon nanochips. These carbon nanochips are themselves comprised of a plurality of graphite platelets, also sometimes called graphite sheets, that are aligned, perpendicular, or at an angle to the longitudinal (growth) axis of the nanofiber. By "at an angle" we mean that the graphite platelets are aligned so that they are neither parallel nor perpendicular to the longitudinal (growth) axis of the nanofiber. For example, they can be from about 1° to about 89°, preferably from about 10° to about 80°, more preferably from about 20° to about 70°, and most preferably from about 30° to about 60° with respect to the longitudinal axis of the nanofiber. In the case where the graphitic sheets are oriented substantially perpendicular to the growth axis, the graphite nanofibers are sometimes referred to as "platelet". In the case where the graphitic sheets are oriented at an angle, to the growth axis are sometimes referred to as "herringbone". The term "carbon" is sometimes used interchangeably with "graphite" herein and the words "nanostucture", "nanofiber", and nanochip are sometimes used interchangeably herein.

The modified graphite nanofibers of the present invention are novel materials having a unique set of properties that include: (i) a surface area from about 20 to 50 m$^2$/g, preferably from about 30 to 45 m$^2$/g, more and most preferably from about 35 to 40 m$^2$/g, which surface area is determined by $N_2$ adsorption at −196° C.; (ii) a crystallinity from about 5% to about 100%, preferably from about 50% to 100%, more preferably from about 75% to 100%, most preferably from about 90% to 100%, and ideally substantially 100%; (iii) an average pore size from about 10 to 15 nm, most preferably from about 11 to 13 nm and ideally 12 nm; (iv) interstices of about 0.335 nm to about 0.40 nm, preferably about 0.335 nm; and (v) unexpectedly high electronic properties as supports for certain catalytic chemical reactions. The interstices are the distance between the graphite platelets. The over all shape of the nanofibers can be any suitable shape. Non-limiting examples of preferred shapes include straight, branched, twisted, spiral, helical, and coiled.

The modified graphite nanofiber catalysts of the present invention can be catalytically grown from suitable unsupported metal powders in a carbon containing atmosphere. A carbon-containing compound is decomposed in a reaction zone in the presence of the metal powder catalyst at temperatures from about 450° C. to about 800° C., preferably from about 550° C. to about 700° C. It is preferred that hydrogen be present during the decomposition of the carbon-containing compound. The modified graphite nanofibers of the present invention are treated in an inert gas environment to a temperature from about 1800° C. to about 3000° C., preferably from about 2300° C. to about 3000° C. Preferred inert gases are helium and argon with helium being more preferred. This high temperature heat treatment gives the modified graphite nanofibers of the present invention their unexpectedly improved catalytic properties when compared to similar graphite nanofibers that were not subjected to high temperature heat treatment.

Metal powdered catalysts suitable for growing the precursor graphite nanofibers of the present invention include single metals, as well as alloys and multi-metallics. If the metal catalyst is a single metal then it is preferably a Group VIII metal selected from Fe, Ni, and Co. If the catalyst is an alloy or multi-metallic material, then it is preferred that it be comprised of a first metal component that will be one or more Group VIII metals and a second metal that is preferably one or more Group IB metals, such as Cu, Ag, and Au. Preferred are Cu and Ag with Cu being the most preferred. It will be understood that Zn can be used in place of one or more of the Group VIII metals. The Group IB metals are present in an amount ranging from about 0.5 to 99 at. % (atomic %). For example, the catalyst can contain up to about 99 at. %, even up to about 70 at. %, or even up to about 50 at. %, preferably up to about 30 at. %, more preferably up to about 10 at. %, and most preferably up to about 5 at. % copper, of Group IB metal with the remainder being a Group VIII metal, preferably nickel or iron, more preferably iron.

Catalysts having a high copper content (70 at. % to 99 at. %) will typically generate nanofibers that are predominantly helical or coiled, and which have a relatively low crystallinity (from about 5 to 25%). Lower concentrations of copper, e.g., 0.5 to 30 at. % have a tendency to produce spiral and branched nanofibers, whereas a catalyst with about 30 to 70 at. %, preferably 30 to 50 at. % copper will produce predominantly branched nanofibers. A third metal can also be present. There is no limitation with respect to what the particular third metal can be as long as it is not deleterious to the desired end product nanofiber. It is preferred that the third metal, if used, be selected from the group consisting of Ti, W, Sn and Ta. When a third metal is present, it is substituted for up to about 20 at. %, preferably up to about 10 at. %, and more preferably up to about 5 at. %, of the second metal. It is particularly preferred that the catalyst be comprised of Cu in combination with Fe, Ni, or Co. More preferred is Cu in combination with Fe and/or Ni from an economic point of view. A catalyst of which Fe is used in place of some of the Ni would be less expensive than a catalyst comprised of Cu in combination with only Ni. Preferred catalysts for producing graphite nanofibers wherein the platelets are substantially perpendicular to the longitudinal axis of the nanofiber are Fe and Fe/Cu multi-metallics. Preferred catalysts for producing graphite nanofibers wherein the graphite platelets are at an angle, other than 90 degrees, from the growth axis, are Fe, Fe/Cu multi-metallics, Fe/Ni multi-metallics, and Ni/Cu multi-metallics. The preferred temperature range for growing "platelet" graphite nanofibers is from about 550° to about 650° C., more preferably from about 575° to about 625° C. The preferred temperature range for growing the angled "herringbone" graphite nanofibers is from about 550° to about 580° C.

Any suitable method can be used to produce the powdered metal catalyst for growing the precursor graphite nanofibers of the present invention. As previously mentioned, it is most preferred in the practice of the present invention that the graphite nanofibers be grown from unsupported metallic powders. A preferred method for preparing suitable unsupported metal catalytic powders is the use of colloidal techniques for precipitating them as metal oxides, hydroxides, carbonates, carboxylates, nitrates, etc. Such a process typically involves dissolving salts of each metal of the catalyst in an appropriate solvent, preferably water. A suitable precipitating agent, such as an ammonium carbonate, ammonium bicarbonate or ammonium hydroxide is added to the solution, thereby causing the metal to precipitate out as the corresponding metal carbonate or hydroxide. The precipitate is then dried at a temperature greater than about 100° C., preferably from about 105° C. to about 120° C., and more preferably at about 110° C. After drying, the precipitate is mixed with a suitable dispersing agent and calcined at a temperature from about 200° to 400° C., preferably from about 2000 to about 300° C., thereby converting the individual metals to their respective oxide form. The milled metal powder mixture is then heated, in a hydrogen-containing atmosphere, at a temperature from about 400° to about 600° C., preferably from about 450° to 550° C., for an effective amount of time, to produce the catalyst in its metallic state. By effective amount of time, we mean that amount of time needed to reduce substantially all of the metal oxides to the respective metal or alloy having a suitable particle size. A typical amount of time will generally be from about 15 to 25 hours. Suitable particle sizes are from about 2.5 nm to about 150 nm, preferably from about 2.5 nm to about 100 nm, and more preferably from about 2.5 nm to about 20 nm. Following this treatment the chemically reduced catalyst is cooled to about room temperature in a helium environment before being passivated in a 2% oxygen/helium mixture for 1 hour at about room temperature (24° C.).

Salts of the catalytic metals used for growing the precursor (initial) graphitic nanofibers of the present invention are salts that are soluble in water, organic solvents, and diluted mineral acids. Non-limiting examples of water-soluble salts suitable for use herein include nitrates, sulfates and chlorides. Non-limiting examples of preferred salts soluble in organic solvents, which are suitable for use herein, include formates, acetates, and oxalates. Non-limiting examples of organic solvents that are suitable for use herein include alcohols, such as methanol, ethanol, propanol, and butanol; ketones, such as acetone; acetates and esters; and aromatics, such as benzene and toluene.

Carbon-containing compounds suitable for establishing an environment wherein the precursor graphitic nanofibers of the present invention are grown are compounds comprised primarily of carbon atoms and hydrogen atoms, although carbon monoxide can also be used. The carbon-containing compound, which is typically introduced into the reaction zone in gaseous form, will generally have no more than 8 carbon atoms, preferably no more than 6 carbon atoms, more preferably no more than 4 carbon atoms, and most preferably no more than 2 carbon atoms. Non-limiting examples of such compounds include CO, methane, ethane, ethylene, acetylene, propane, propylene, butane, butene, butadiene, pentane, pentene, cyclopentadiene, hexane, cyclohexane, benzene, and toluene. Combinations of gases are preferred, particularly a mixture of carbon monoxide and ethylene.

It may be desirable to have an effective amount of hydrogen present in the reaction, or growth, zone during nanofiber growth. Hydrogen serves various complementary functions. For example, on the one hand it acts as a reconstruction agent for the catalyst, suppresses the formation of metal carbide that results in deactivation and on the other hand it hydrogasifies, or causes carbon burn-off, of the carbon structure. By an effective amount, we mean that minimum amount of hydrogen that will maintain a clean catalyst surface (free of carbon residue), but not so much that will cause excessive hydrogasification, or burn-off, of carbon from the nanofibers and/or substrate structure, if present. Generally, the amount of hydrogen present will range from about 5 to 40 vol. %, preferably from about 10 to 30 vol. %, and more preferably from about 15 to 25 vol. %. For some catalyst systems, such as Cu:Fe, the hydrogasification reaction is relatively slow, thus, an effective amount of hydrogen is needed to clean the catalyst in order to keep it clean of carbon residue and maintain its activity. For other catalyst systems, such as Cu:Ni, where the activity is so high that excessive hydrogasification occurs, even at relatively low levels of hydrogen, little, if any, hydrogen is needed in the heating zone. A Cu:Ni catalyst is so active that it utilizes essentially all of the carbon deposited thereon to grow nanofibers, and thus, there is generally no carbon residue to clean off.

After the carbon nanofibers are grown, it is required to heat the final structure in an inert gas at temperatures up to about 3000° C., preferably from about 1800° C. to about 3000° C., and more preferably from about 2300° C. to about 3000° C. Under these conditions up to 50% of the adjacent edges of the nanofibers undergo a sealing action to form the type of nanochip structure of the present invention.

While a standard incipient wetness technique can be used to introduce the desired catalytic metal or metal oxide precursor salt, this operation must be conducted in non-aqueous media. This is because, in the "as-prepared condition" the carbon nanochips are hydrophobic in nature and poor metal/metal oxide dispersion is achieved if one uses water as the solvent. Electrochemical reduction methods can also be used to deposit the desired catalytic species onto the nanochips. It is also necessary to select a metal precursor salt that undergoes oxidation at a relatively low temperature in order to avoid gasification of the nanofiber support during the calcinations step. For the same reasons a corresponding set of precautions must also be followed in cases where reduction to the metallic state in hydrogen is carried out. With these safeguards no loss of support material is recorded during the catalyst preparation procedure.

The carbon nanochips of the present invention can be used to support any metal or metal oxide suitable for use in heterogeneous catalytic reactions. Non-limiting heterogeneous catalytic reactions for which the instant nanochips can be used as catalyst support materials include oxidation, hydrogenation, reforming, steam reforming, oxidative dehydrogenation, dehydrogenation, isomerization, carbonylation, decarbonylation and electro-catalytic reactions.

Below is a first table setting forth preferred hydrogenation reactions along with the typical catalytic metal used and reaction conditions employed.

| HYDROGENATION REACTIONS | | | |
|---|---|---|---|
| Reaction | Catalyst | Temperature Range (° C.) | Pressure (atm) |
| Benzene to cyclohexane | Ni | 180-230 | 20-50 |
| Nitrobenzene to Aniline | Pd, Pt | 50-150 | 1-5 |
| Reductive alkylation of nitroaromatics | Pt | ~50 | ~1 |
| Nitriles to amines | Co, Ru, Ni | 80-200 | 20-170 |
| Hydrogenation of fats & oils | Ni | 120-175 | 1-2 |

Below is a first table setting forth preferred oxidation reactions along with the typical catalytic metal used and reaction conditions employed.

OXIDATION REACTIONS

| Reaction | Catalyst | Temperature Range (° C.) | Pressure (atm) |
|---|---|---|---|
| Sulfur dioxide to sulfuric acid | $V_2O_5/K_2O$ | 420-480 | ~1 |
| Ethylene to ethylene oxide | Ag | 200-250 | ~8 |
| Ethylene to vinyl acetate | Pd | 10-130 | 30 |
| Propylene to acrolein | $Bi_2O_3/Mo_2O_3$ | 320-430 | 2 |

Preferred metals to be supported on the modified graphite nanofibers are the transition metals; more preferred are the Group VIII metals. The Group VIII metals can be either non-noble, such as Ni, Co and Fe or the noble metals such as Pt, Pd, Rh, Ir, Ru and Re, and mixtures thereof. Other metals include those in Groups IB and IIB, such as Cu, Ag, Au, Zn and Cd and mixtures thereof. The concentration of metal on the carbon nanochip support will be an effective amount. That is, at least that amount that will produce the desired catalytic effect. The concentration will typically be from about 0.1 wt. % to about 30 wt. %, preferably from about 1 wt. % to about 20 wt. %, based on the total weight of carbon nanochip plus metal.

Preferred metal oxides are the transition metal oxides, $V_2O_5$, $MoO_3$, $Bi_2O_3$, $TiO_2$, $Fe_2O_3$, FeO, $Cr_2O_3$, MgO, CuO, ZnO and mixtures thereof. The concentration of metal oxide on the carbon nanochip support will be an effective amount. That is, at least that amount which will produce the desired catalytic effect. The concentration will typically be from about 0.1 wt. % to about 30 wt. %, preferably from about 1 wt. % to about 20 wt. %, based on the total weight of carbon nanochip plus metal oxide.

Furthermore, the carbon nanochip catalyst support system of the present invention may also contain the metals and/or alloy particles inserted between two adjacent graphite sheets within the nanochip, a configuration that will effectively prevent particle sintering due to mobility, coalescence and growth. This catalyst arrangement will allow for selected molecules to be dissociated on the catalyst and for selected products to diffuse out of the graphite nanofiber structure into the gas phase.

This invention will be illustrated in more detail with reference to the following examples that should not be construed to be limiting the scope of the invention.

EXAMPLES

General Conditions

The preferred precursor graphite nanofibers of the present invention were prepared from the Cu—Fe (3:7) catalyzed decomposition of a $CO/H_2$ (4:1) mixture at 600° C. according to the method described in U.S. Pat. No. 6,537,515 B1 to Baker et al. Prior to use as a support medium the graphite nanofibers were treated at temperatures up to 2330° C. in argon to form the corresponding nanochips.

Silver was introduced onto the respective nanochips and alpha-alumina via a conventional incipient wetness technique using silver nitrate as the precursor salt dissolved in ethanol. The concentration of the silver salt was calculated so as to produce a final catalyst containing 10 wt. % of the metal on each type of support medium. The impregnated support materials were calcined in flowing air at 250° C. for 4 hours in order to convert the silver salt to the metal oxide state and then reduced in 10% $H_2$/He mixture at 300° C. for 20 hours. The reduced catalyst samples were passivated in 2% $CO_2$/He at room temperature before removal from the reactor.

In one series of comparative experiments 0.1 gram of 10 wt. % Ag/carbon "platelet" nanochips was placed in a 1.0-inch internal diameter, vertical quartz reactor system. The performance of the carbon nanochip supported silver for the partial oxidation of ethylene to ethylene oxide was compared to that of an industrial catalyst consisting of Ag dispersed on alpha-alumina. The samples were heated at a temperature of 220° C. in the presence of a $C_2H_4/O_2$ (1:4) mixture at a flow rate of 27.5 cc/min for various periods of time. An on-line gas chromatography unit was used to determine the concentrations of gaseous products together with unconverted reactants.

The characteristics and sizes of the silver particles dispersed on the various support media were determined by high-resolution transmission electron microscopy. These examinations were conducted in a JEOL 2000 EXII instrument equipped with a high-resolution pole piece capable of giving a lattice resolution of 0.18 nm. Surface area and pore size measurements were carried out in a Micrometrics Tristar unit using nitrogen adsorption at −196° C.

The gases used in these examples were carbon monoxide (99.9%), ethylene (99.95%); hydrogen (99.999%), helium (99.99%) and argon (99.99%) were purchased from Air Products and dried before use. Reagent grade iron nitrate and copper nitrate were used in the preparation of catalysts for precursor graphite nanofiber growth and silver nitrate for catalysts for ethylene oxidation reactions. These chemicals were obtained from Fisher Scientific.

Example 1

The data given in Table I below shows the comparison of some of the physical characteristics of various support materials, including the current commercial system based on alpha-alumina that is used for the Ag catalyzed partial oxidative of ethylene to ethylene oxide at 220° C. The three carbon nanochips were heat treated at the three different temperatures of 2800° C., 2330° C. and 1800° C.

TABLE I

| Catalyst Support | S.A. ($m^2/g$) | Pore Size (nm) |
|---|---|---|
| Carbon Nanochips (2800° C.) | 28 | 15.2 |
| Carbon Nanochips (2330° C.) | 40 | 13.2 |
| Carbon Nanochips (1800° C.) | 50 | 11.8 |
| Platelet Graphite Nanofibers | 80 | 6.3 |
| alpha-alumina | 4 | 5.9 |

Examination of the results showed some significant features and highlights the gradual transformation in physical properties of the "platelet" GNF that had been treated in argon at high temperatures. While the surface area exhibits a gradual decrease as a function of treatment temperature, there is a concomitant increase in the average pore size.

Example 2

In this series of experiments 102 mg of 10 wt. % Ag supported on carbon nanochips produced from platelet graphite nanofibers that had been treated in Ar at 2330° C. were reacted in a $C_2H_4/O_2$ (1:4) mixture at 220° C. for 3 days. The product distribution, $C_2H_4$ conversion and selectivity towards the desired product, ethylene oxide, were measured at regular intervals of this period of time and are presented in Table II.

TABLE II

| Time (hours) | % $C_2H_4$ Conv. | % $C_2H_4O$ selectivity | % $C_2H_4O$ yield |
|---|---|---|---|
| 0.53 | 67.57 | 84.87 | 57.35 |
| 1.56 | 66.08 | 85.95 | 56.79 |
| 3.58 | 75.30 | 90.68 | 68.28 |
| 5.61 | 77.20 | 91.42 | 70.57 |
| 6.83 | 77.33 | 91.33 | 70.62 |
| 8.24 | 74.00 | 91.17 | 67.46 |
| 12.43 | 74.68 | 91.96 | 68.67 |
| 13.31 | 76.18 | 92.22 | 70.25 |
| 30.43 | 76.81 | 93.15 | 71.55 |
| 35.40 | 68.01 | 89.23 | 60.69 |
| 37.40 | 74.75 | 92.12 | 68.86 |

Inspection of these data indicates that this catalyst system maintains its high activity for a prolonged period of time and gives a very high selectivity towards ethylene oxide.

Example 3

A comparison set of experiments was carried out using the current commercial catalyst system, which consisted of 101 mg of 10 wt. % Ag supported on alpha-alumina reacted in a $C_2H_4/O_2$ (1:4) mixture at 220° C. for 5 days. The product distribution, $C_2H_4$ conversion and selectivity towards the desired product, ethylene oxide, were measured at regular intervals of this period of time and are presented in Table III below.

TABLE III

| Time (hours) | % $C_2H_4$ Conv. | % $C_2H_4O$ selectivity | % $C_2H_4O$ yield |
|---|---|---|---|
| 1.50 | 33.78 | 84.40 | 28.51 |
| 2.67 | 34.60 | 84.19 | 29.13 |
| 3.54 | 37.84 | 84.73 | 32.06 |
| 4.52 | 38.22 | 84.74 | 32.38 |
| 22.82 | 37.11 | 86.35 | 32.05 |
| 27.31 | 39.97 | 86.32 | 34.50 |
| 29.04 | 40.31 | 86.25 | 34.77 |
| 52.04 | 41.00 | 86.33 | 35.40 |
| 71.54 | 38.56 | 85.54 | 32.98 |
| 75.62 | 39.98 | 86.00 | 34.38 |
| 78.72 | 40.21 | 85.97 | 34.57 |
| 94.57 | 39.17 | 85.66 | 33.56 |
| 97.57 | 40.44 | 85.76 | 34.69 |
| 102.40 | 39.78 | 85.36 | 33.96 |

It is evident that while this catalyst system maintains its activity and selectivity for a prolonged period of time the overall performance is about a factor of 2 lower than that of the Ag/graphite nanofiber (2330° C.) catalyst system presented in Example 2.

Example 4

In a further series of experiments 102 mg of 10 wt. % Ag supported on high purity "platelet" graphite nanofibers (not treated at high temperatures) were reacted in a $C_2H_4/O_2$ (1:4) mixture at 220° C. for 5 days. The product distribution, $C_2H_4$ conversion and selectivity towards the desired product, ethylene oxide, were measured at regular intervals of this period of time and are given in Table IV below.

TABLE IV

| Time (hours) | % $C_2H_4$ Conv. | % $C_2H_4O$ selectivity | % $C_2H_4O$ yield |
|---|---|---|---|
| 1.48 | 15.40 | 87.85 | 13.53 |
| 2.52 | 16.64 | 89.16 | 14.84 |
| 3.73 | 16.92 | 89.13 | 15.08 |

TABLE IV-continued

| Time (hours) | % $C_2H_4$ Conv. | % $C_2H_4O$ selectivity | % $C_2H_4O$ yield |
|---|---|---|---|
| 4.63 | 17.99 | 90.36 | 16.25 |
| 6.67 | 19.77 | 91.50 | 18.09 |
| 23.92 | 24.34 | 92.41 | 22.49 |
| 26.15 | 25.94 | 91.81 | 23.82 |
| 30.13 | 26.85 | 92.07 | 24.72 |
| 47.95 | 30.96 | 92.73 | 28.71 |
| 71.95 | 33.32 | 93.09 | 31.02 |
| 75.98 | 37.88 | 92.95 | 35.21 |
| 97.60 | 37.65 | 93.05 | 35.03 |

Examination of these data reveals that the catalyst reaches its optimum selectivity within the first 24 hours on stream. In contrast, catalytic activity exhibited a progressive increase reaching a maximum level after 75 hours reaction, indicating the existence of a significant induction period. Comparison of the behavior of this system with that of the Ag/alpha-alumina shows that comparable performances are achieved after about 75 hours on stream.

Example 5

In another series of experiments 103 mg of 10 wt. % Ag supported on high purity multi-walled carbon nanotubes were reacted in a $C_2H_4/O_2$(1:4) mixture at 220°C. for 2 days. The product distribution, $C_2H_4$ conversion and selectivity towards the desired product, ethylene oxide, were measured at regular intervals of this period of time and are given in Table V below.

TABLE V

| Time (hours) | % $C_2H_4$ Conv. | % $C_2H_4O$ selectivity | % $C_2H_4O$ yield |
|---|---|---|---|
| 0.43 | 17.53 | 87.04 | 15.26 |
| 1.53 | 18.61 | 88.61 | 16.49 |
| 2.60 | 19.91 | 89.01 | 17.72 |
| 3.80 | 18.14 | 89.07 | 16.16 |
| 4.92 | 18.93 | 90.81 | 17.19 |
| 6.12 | 19.32 | 90.57 | 17.50 |
| 23.59 | 17.50 | 89.79 | 15.72 |
| 24.66 | 16.35 | 89.34 | 14.61 |
| 25.53 | 17.88 | 90.03 | 16.10 |
| 27.56 | 17.78 | 88.64 | 15.76 |
| 29.24 | 18.17 | 89.32 | 16.23 |

It is evident from the above Table that while the selectivity towards ethylene oxide is superior to that of the Ag/alpha-alumina catalyst, the overall activity is significantly below that of the modified graphite nanofibers catalyst systems of the present invention. In this respect one can conclude that the arrangement and nature of the graphite sheets constituting the carbon nanostructures is a key factor in determining the performance of Ag particles dispersed on such materials.

Example 6

In this set of experiments 101 mg of 10 wt. % Ag supported on high purity graphite flakes were reacted in a $C_2H_4/O_2$ (1:4) mixture at 220° C. for 2 days. The product distribution, $C_2H_4$ conversion and selectivity towards the desired product, ethylene oxide, were measured at regular intervals of this period of time and are given in Table VI below.

TABLE VI

| Time (hours) | % C$_2$H$_4$ Conv. | % C$_2$H$_4$O selectivity | % C$_2$H$_4$O yield |
| --- | --- | --- | --- |
| 1.40 | 18.62 | 82.68 | 15.40 |
| 2.55 | 18.69 | 84.00 | 15.70 |
| 3.68 | 16.86 | 81.95 | 13.81 |
| 4.61 | 17.95 | 82.22 | 14.76 |
| 5.54 | 18.34 | 83.49 | 15.31 |
| 6.56 | 18.12 | 83.45 | 15.12 |
| 7.38 | 17.49 | 82.74 | 14.47 |
| 27.67 | 17.84 | 83.04 | 14.82 |
| 28.54 | 16.81 | 81.69 | 13.73 |
| 30.04 | 15.75 | 80.26 | 12.64 |

From these data one can see that the high selectivity and superior overall catalytic activity observed with the high-temperature treated "platelet" graphite nanofibers are not attained when silver particles are dispersed on a traditional graphite support.

Example 7

In a final series of experiments the 200 mg of the support materials, "platelet", high-temperature heat-treated "platelet" and multi-walled carbon nanotubes were reacted in the absence of metal particles in a C$_2$H$_4$/O$_2$ (1:4) mixture at temperatures ranging from 220 to 400° C. for periods of up to 1 day. In none of these systems was it possible to detect the presence of ethylene oxide in the products. One may confidently conclude that these materials do not function as catalysts in their own right for the ethylene epoxidation reaction.

What is claimed is:

1. A catalytic chemical process selected from oxidation, hydrogenation, and electro-catalytic reactions, which is catalyzed by a catalyst composition comprised of at least one metal or metal oxide selected from the metals from Groups VIII, IB, and IIB of the Periodic Table of the Elements, supported on graphitic nanofibers which nanofibers are comprised of a plurality of graphite platelets aligned substantially perpendicular, or at an angle, other than parallel, to the longitudinal axis of the nanofibers and wherein at least about 50% of the edge sites of said nanofibers are exposed, wherein said graphite nanofibers, prior to supporting said at least one metal of metal oxide, are heat treated in the presence of an inert gas at temperatures from about 2300° C. to about 3000° C.

2. The catalytic chemical process of claim 1 wherein the platelets are aligned substantially 90° with respect to the longitudinal axis of the nanofiber.

3. The catalytic chemical process of claim 1 wherein the platelets are aligned at angle from about 30° to about 60° with respect to the longitudinal axis of the nanofibers.

4. The catalytic chemical process of claim 1 wherein the inert gas is selected from helium and argon.

5. The catalytic chemical process of claim 1 which is the oxidation reaction of ethylene to ethylene oxide using silver as the catalytic metal.

* * * * *